United States Patent
Aldalbahi et al.

(10) Patent No.: US 10,793,689 B1
(45) Date of Patent: Oct. 6, 2020

(54) METHOD OF SYNTHESIS OF BIO GRAPHENE FILM

(71) Applicant: KING SAUD UNIVERSITY, Riyadh (SA)

(72) Inventors: Ali Kanakhir Aldalbahi, Riyadh (SA); Manal Ahmed Gasmelseed Awad, Riyadh (SA); Shaykha Mohammed Alzahly, Riyadh (SA); Khalid Mustafa Osman Ortashi, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/409,798

(22) Filed: May 11, 2019

(51) Int. Cl.
| | |
|---|---|
| *B32B 9/00* | (2006.01) |
| *C08J 5/18* | (2006.01) |
| *C08B 37/00* | (2006.01) |
| *C08K 3/04* | (2006.01) |
| *C08J 3/00* | (2006.01) |
| *C08K 11/00* | (2006.01) |
| *B82Y 30/00* | (2011.01) |
| *B82Y 40/00* | (2011.01) |

(52) U.S. Cl.
CPC ............. *C08J 5/18* (2013.01); *C08B 37/0042* (2013.01); *C08J 3/005* (2013.01); *C08K 3/042* (2017.05); *C08K 11/005* (2013.01); *B82Y 30/00* (2013.01); *B82Y 40/00* (2013.01); *C08J 2305/00* (2013.01); *Y10T 428/30* (2015.01)

(58) Field of Classification Search
CPC ........ C01B 31/04; B82Y 30/00; Y10T 428/30
USPC ....................................... 428/408; 423/447.1
See application file for complete search history.

(56) References Cited

U.S. PATENT DOCUMENTS

| | | | |
|---|---|---|---|
| 2011/0062630 A1* | 3/2011 | Honda ................... | A61K 8/731 264/299 |
| 2016/0304778 A1 | 10/2016 | Thalappil | |

FOREIGN PATENT DOCUMENTS

| | | |
|---|---|---|
| CN | 105175800 A | 12/2015 |
| CN | 105315507 A | 2/2016 |
| CN | 105315508 A | 2/2016 |
| CN | 106750571 A | 5/2017 |
| CN | 107325648 A | 11/2017 |
| CN | 107586393 A | 1/2018 |

OTHER PUBLICATIONS

High Performance of Artificial Nacre-Like Graphene Oxide-Carrageenan Bio-nanocomposite Films, Zhu, Materials, 10, 536, p. 1-11, 2017.*
Purkait, T., et al., "Large area few-layer graphene with scalable preparation from waste biomass for high-performance supercapacitor," Scientific Reports (7) pp. 1-14 2017.

(Continued)

*Primary Examiner* — Daniel H Miller
(74) *Attorney, Agent, or Firm* — Nath, Goldberg & Meyer; Richard C. Litman

(57) ABSTRACT

The method of synthesis of bio graphene may include mixing carrageenan with a bio waste solution, adding graphene oxide to produce a mixture, sonicating the mixture, and evaporative-casting the mixture to produce bio graphene film. In an embodiment, the carrageenan may be τ-carrageenan. In an embodiment, the bio waste solution may include fish scales.

4 Claims, 7 Drawing Sheets

(56) References Cited

OTHER PUBLICATIONS

Tang, L., et al., "7 Graphene/Polymer Composite Materials: Processing, Properties, and Applications," Advanced Composite Materials: Properties and Applications, 2017.

Mohan, S., et al., "Biopolymers—Application in Nanoscience and Nanotechnology," InTech, 2016.

Khan, Z. U. et al., "A Review of Graphene Oxide, Graphene uckypaper, and Polymer/Graphene Composites: Properties and Fabrication Techniques," Polymer-Plastics Technology and Engineering (55)6: pp. 559-581, 2016.

Sayyar, S., "The development of graphene/biocomposites for biomedical applications," U. of Wollongong Thesis Collection, 2014.

* cited by examiner

METHOD OF SYNTHESIS OF BIO GRAPHENE FILM

BACKGROUND

1. Field

The disclosure of the present patent application relates to graphene-biopolymer synthesis, and particularly to a method of synthesis of a bio graphene film using carrageenan and fish scales.

2. Description of the Related Art

Graphene is an allotrope of carbon consisting of a single layer of carbon atoms arranged in a hexagonal lattice. Graphene has unique strength, conductivity, and magnetic properties. Recently, there has been significant interest in the production of graphene-polymer composite materials. Graphene has been incorporated into a number of polymer composites, including epoxy, polystyrene, polypropylene, and the like. However, many of these graphene polymer composites rely upon fossil fuel-derived polymers. The use of fossil fuel derived polymers adds to environmental pollution and consumption of a non-renewable resource.

Thus, a method of synthesis of bio graphene film solving the aforementioned problems is desired.

SUMMARY

The method of synthesis of bio graphene may include mixing carrageenan with a bio waste solution, adding graphene oxide to produce a mixture, sonicating the mixture, and evaporative-casting the mixture to produce bio graphene film. In an embodiment, the carrageenan may be τ-carrageenan. In an embodiment, the bio waste solution may include fish scales. The resulting bio graphene film may be particularly useful for formulating gasoline containers or manufacturing plastic containers for preserving foodstuffs.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
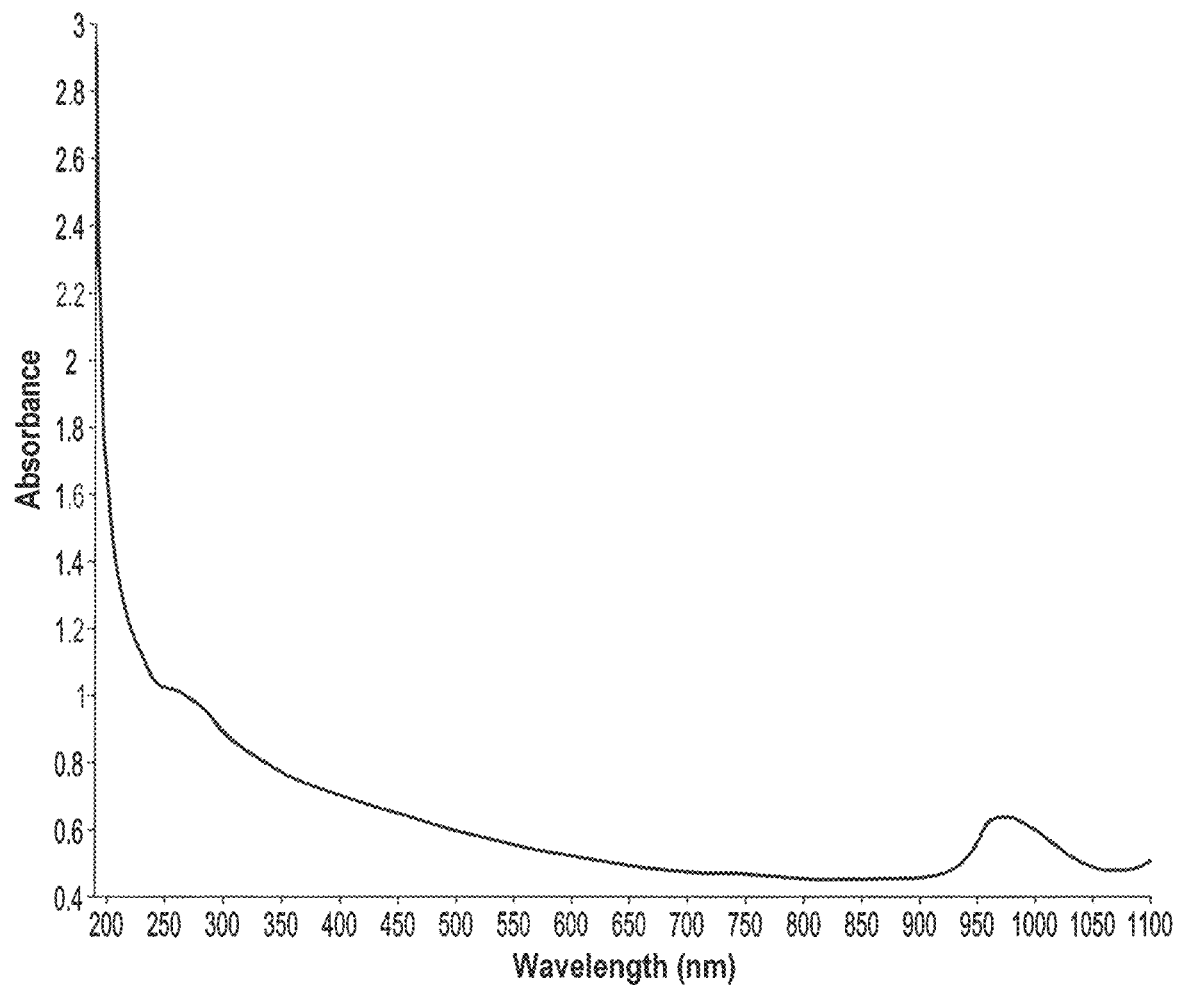
FIG. 1 depicts an ultraviolet spectrum of a bio graphene film produced with τ-carrageenan and fish scales according to the present teachings.
Figure 2:
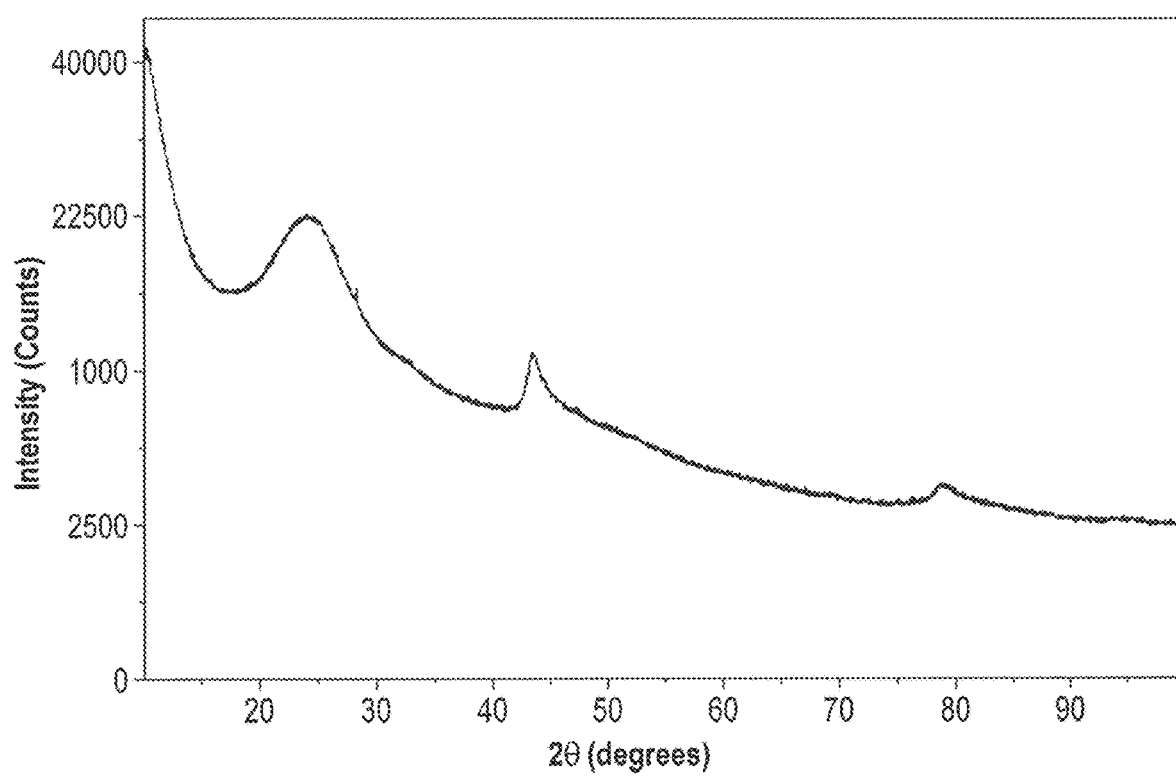
FIG. 2 depicts an X-ray diffraction spectrum of the bio graphene film produced with τ-carrageenan and fish scales.

A method of synthesis of bio graphene may include mixing carrageenan with a bio waste solution, adding graphene oxide to produce a mixture, sonicating the mixture, and evaporative-casting the mixture to produce bio graphene film. In an embodiment, the carrageenan may be τ-carrageenan. In an embodiment, the bio waste solution may include fish scales.

As used herein, the term "about," when used to modify a numerical value, means within ten percent of that numerical value.

Fish scales are a bio waste material produced when fish are prepared for human consumption. The present method facilitates recycling bio waste to reduce the impact of landfills or other bio waste disposal mechanisms on the environment. The bio waste may be derived from fish scales. The fish scales may be waste fish scales. In an embodiment, fish scales can be reduced to a powder form, herein "powdered fish scales." In an embodiment, about 30 mg to about 75 mg of the powdered fish scales may be suspended in a boiling solution of about 15 ml to about 50 ml ethanol and deionized water (1:9 v/v), to produce the bio waste solution.

In an embodiment, the fish scales may be scales of the Nile Tilapia, *Oreochromis niloticus*. The fish scales may be washed thoroughly, dried, and ground to a fine powder before use.

Carrageenan is a biopolymer commonly extracted from Rhodophyta (red seaweed). The carrageenan can include at least one of Kappa-carrageenan, iota-carrageenan, and lambda-carrageenan. These types of carrageenan are distinguished by their degree of sulfation. Kappa-carrageenan has a single sulfate group per disaccharide, while iota-carrageenan has two, and lambda-carrageenan has three. In an embodiment, the carrageenan may be iota carrageenan. In a further embodiment the iota carrageenan may be τ-carrageenan.

The following examples illustrate the present teachings.

Example 1

Preparation of Bio Graphene Film

Nile Tilapia were collected from Khartoum, Sudan, and their scales were washed and removed. The free scales were then washed a second time, dried, and ground to a fine powder. A bio waste solution was prepared by mixing 10 ml ethanol and 90 ml deionized water (1:9 v/v), boiling the mixture, and adding about 75 mg powdered fish scales to the mixture to produce the bio waste solution. About 120 mg τ-carrageenan (IC) was then added to about 15 ml of the bio waste solution and stirred for about 3 hours at about 70° C. to produce a biopolymer/bio waste mixture. Graphene oxide (about 150 mg) was then added to the biopolymer/bio waste mixture, and sonicated with a digital sonicator with a probe diameter of 10 mm, in pulse mode (0.5 s on/off), with an ultrasonic power of 750 W, and a frequency of 20 kHz, to produce a carrageenan/fish scale/graphene dispersion. During sonication, the dispersion was maintained at a constant temperature by placing it in a water bath. The dispersion was then used to prepare a bio graphene film by evaporative-casting in petri dishes and drying in the oven at 35° C. for about 24 hours.

Example 2

Analysis of the Bio Graphene Dispersion

The ultraviolet-visible-absorption spectra of the bio graphene dispersion created according to the method of Example 1 shows an absorption peak at 250-300 nm (FIG. 1).

Example 3

Analysis of the Bio Graphene Film

An x-ray diffraction spectrum of the bio graphene film shows two peaks that reference to graphene, a weak and broad peak at approximately 2θ=25.00, corresponding to the (002) diffraction plane of graphene, and a narrow peak at 2θ=430, corresponding to the crystal of (002) plane. Iota-carrageenan is also known to have a peak at approximately 2θ=25.00.

Figure 3A:
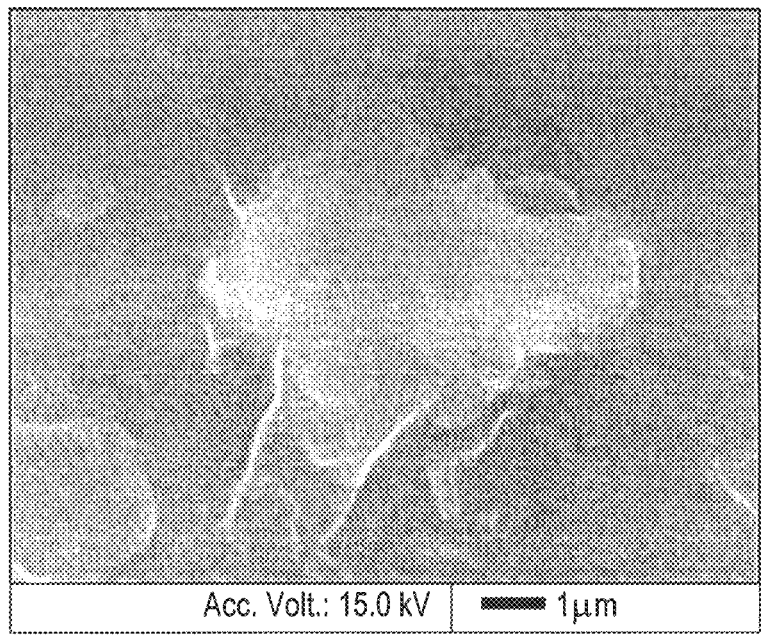
FIG. 3A depicts a scanning electron micrograph of the bio graphene film produced with τ-carrageenan and fish scales.
Figure 3B:
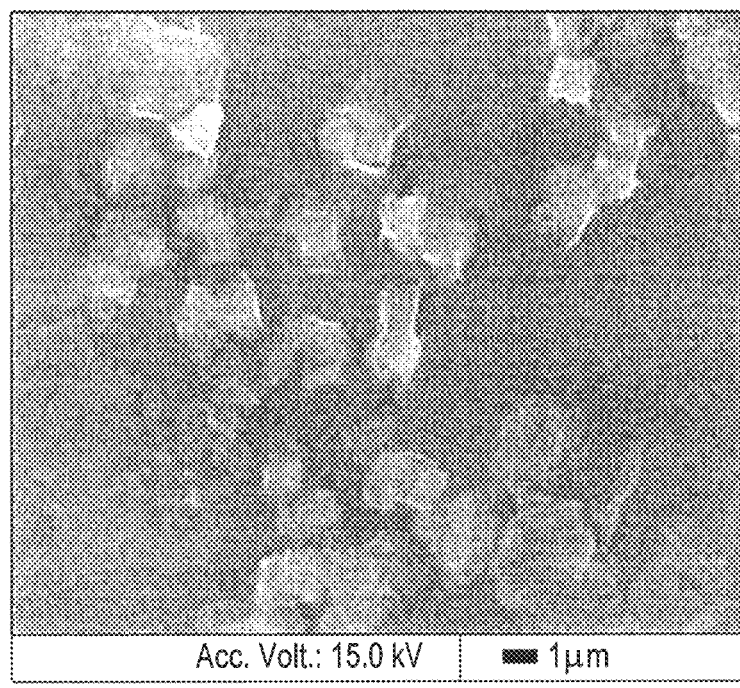
FIG. 3B depicts a scanning electron micrograph of the bio graphene film produced with τ-carrageenan and fish scales.

Scanning electron micrographs of the bio graphene film indicate a porous 3D networked structure with a few folds (FIGS. 3A-3B). FIGS. 3A-3B demonstrate that the graphene oxide nanosheets are homogenously coated by the carrageenan/fish scales, confirming that the carrageenan/fish scales were successfully polymerized on the surfaces of the graphene oxide nanosheets, forming a smooth structure, and the overall morphology of the film is resultantly rougher, with wrinkles associated with the graphene oxide nanosheet structures.

Figure 4A:
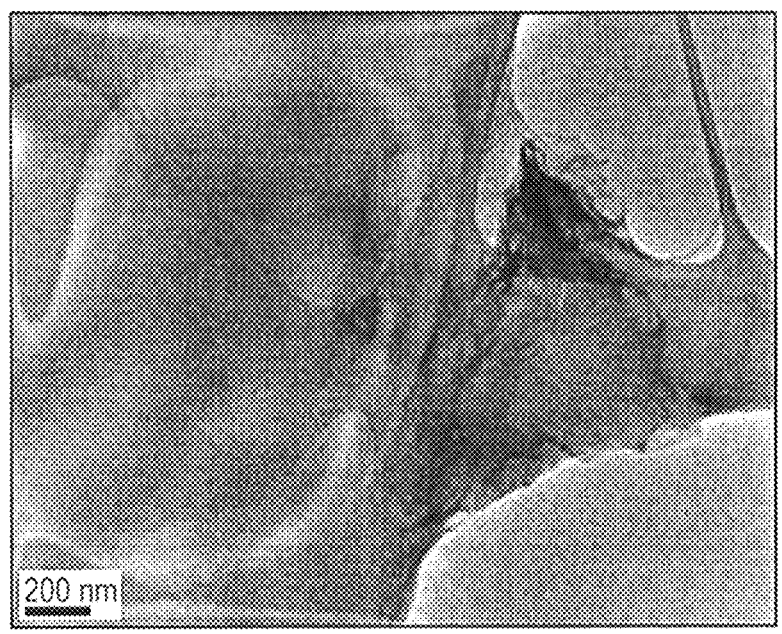
FIG. 4A depicts a transmission electron micrograph of the bio graphene film produced with τ-carrageenan and fish scales.
Figure 4B:
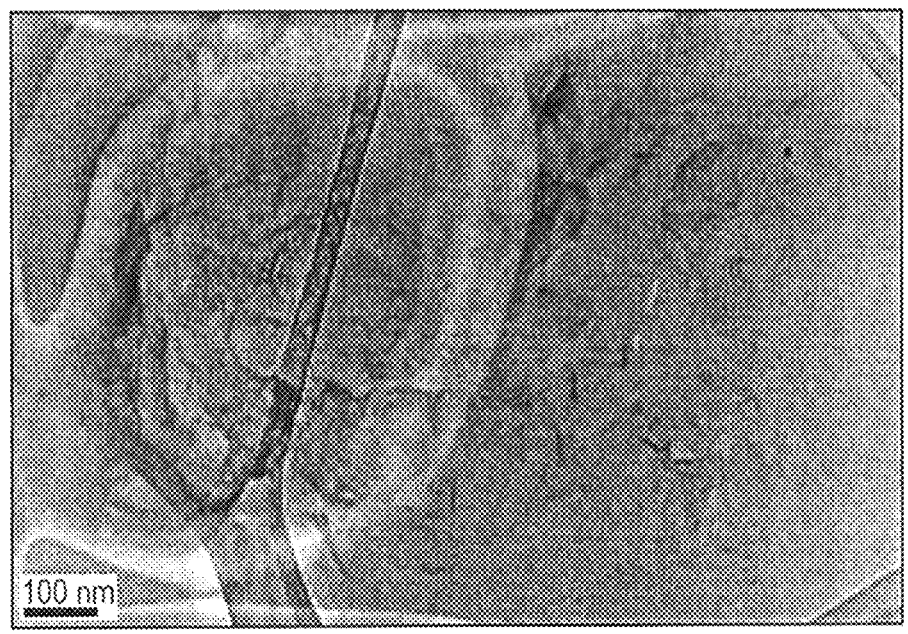
FIG. 4B depicts a transmission electron micrograph of the bio graphene film produced with τ-carrageenan and fish scales.

Transmission electron micrographs of the bio graphene film confirmed the homogenous dispersion of the graphene oxide sheets within the polymer matrix, and the relatively limited number of aggregations of the nanostructures (FIGS. 4A-4B).

Figure 5:
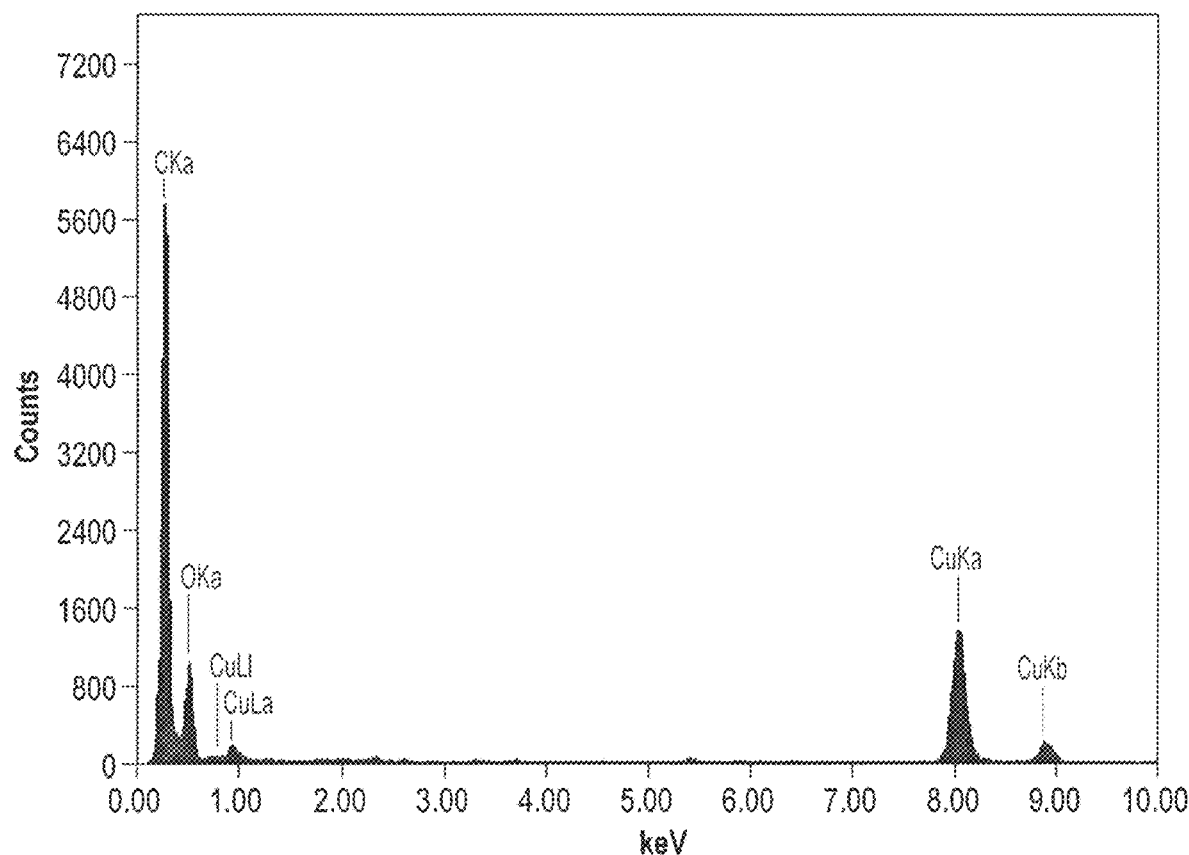
FIG. 5 depicts an energy dispersive X-ray spectrum of the bio graphene film produced with τ-carrageenan and fish scales.

Energy dispersive X-ray spectroscopy of the bio graphene film confirmed the presence of carbon, oxygen, graphene oxide, and polymer (FIG. 5).

Figure 6:
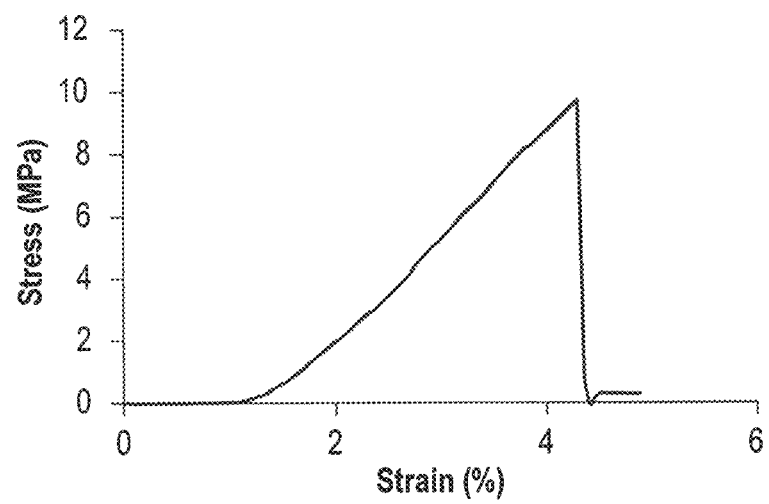
FIG. 6 depicts a stress/strain curve for the bio graphene film produced with τ-carrageenan and fish scales.

The stress-strain curve of the bio graphene film demonstrated that stress linearly increases to 9.7 MPa and reduces at the break point (γ) at 4.2% strain (FIG. 6).

Figure 7:
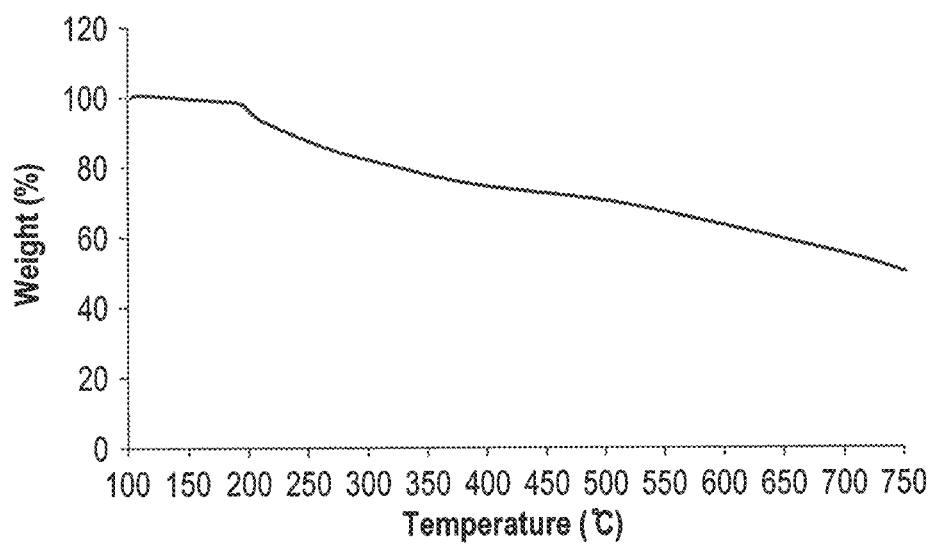
FIG. 7 depicts a thermal gravimetric analysis spectrum of the bio graphene film produced with τ-carrageenan and fish scales.

Thermal gravimetric analysis of the bio graphene film was conducted at temperatures ranging from about 100° C. to about 800° C. As shown in FIG. 7, the bio graphene film experiences a significant weight loss as the temperature increases, resulting in approximately 70% weight loss below 800° C.

Figure 8:
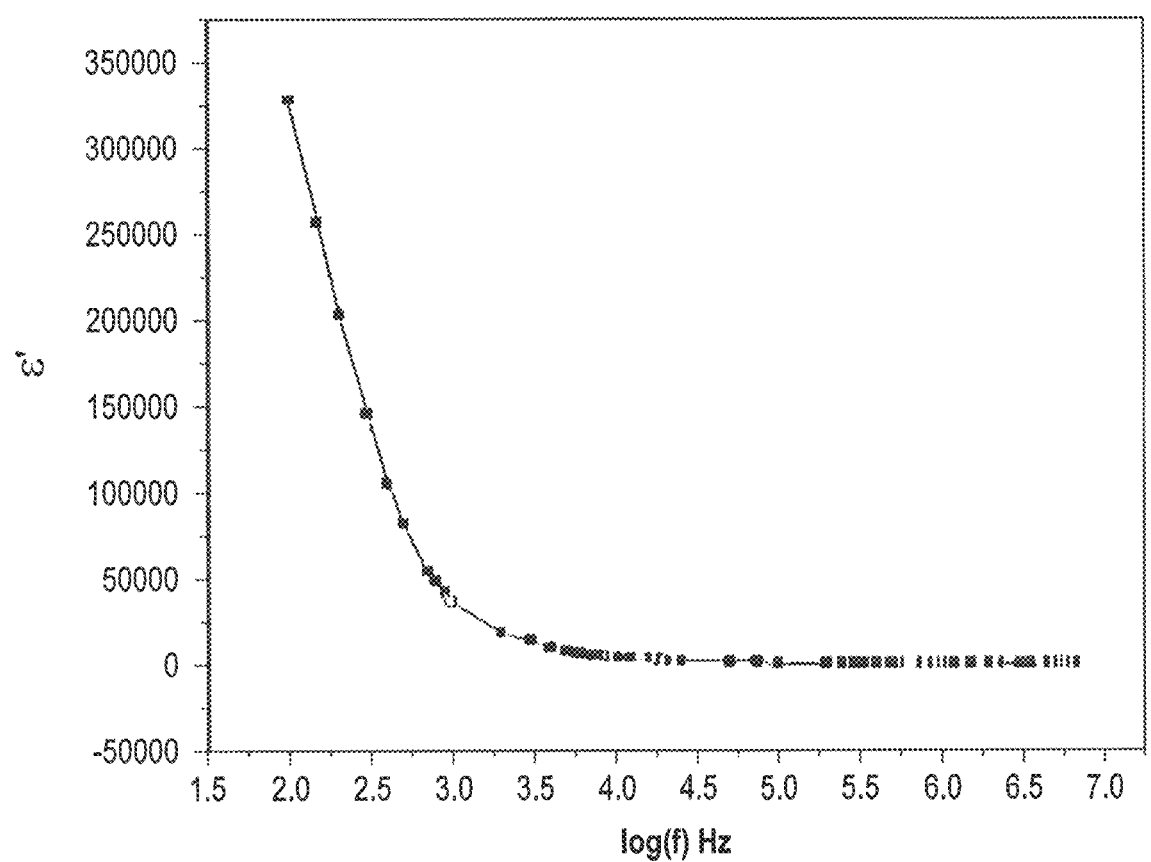
FIG. 8 depicts the variation of the dielectric constant (e') with log frequency for the bio graphene film produced with τ-carrageenan and fish scales.

The dielectric constant of the bio graphene film decreased rapidly with increased frequency (FIG. 8).

It is to be understood that the method of synthesis of bio graphene film is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesis of a bio graphene film, comprising:
synthesizing a bio waste solution from powdered fish scales, wherein the bio waste solution is synthesized by adding about 30 mg to about 75 mg powdered fish scales into a boiling solution of about 15 ml to about 50 ml ethanol and deionized water (1:9 v/v);
mixing a carrageenan with the bio waste solution to provide a first mixture, wherein the carrageenan is selected from the group consisting of Kappa-carrageenan, iota-carrageenan, and lambda-carrageenan;
adding graphene oxide to the first mixture to produce a second mixture;
sonicating the second mixture; and
evaporative-casting the second mixture to produce the bio graphene film.

2. The method of synthesis of the bio graphene film according to claim 1, wherein about 120 mg of the carrageenan is mixed with about 15 ml of the bio waste solution.

3. The method of synthesis of the bio graphene film according to claim 1, wherein the carrageenan is mixed with the bio waste solution by stirring for about 3 hours at about 70° C.

4. The method of synthesis of the bio graphene film according to claim 1, wherein about 150 mg of the graphene oxide is added to the first mixture.

* * * * *